United States Patent [19]

Moriizumi et al.

[11] Patent Number: 5,177,994
[45] Date of Patent: Jan. 12, 1993

[54] ODOR SENSING SYSTEM

[75] Inventors: Toyosaka Moriizumi; Takamichi Nakamoto, both of Tokyo; Atsushi Fukuda, Kanagawa; Yasuo Asakura, Kyoto, all of Japan

[73] Assignee: Suntory Limited and Tokyo Institute of Technology, Japan

[21] Appl. No.: 704,112

[22] Filed: May 22, 1991

[51] Int. Cl.$^5$ .............................................. G01N 31/00
[52] U.S. Cl. ..................... 73/23.340; 422/83
[58] Field of Search ............... 73/23.34; 422/83, 88

[56] References Cited

U.S. PATENT DOCUMENTS 4,770,027  9/1988  Ehara et al. ..................... 73/23.34

FOREIGN PATENT DOCUMENTS 0282332  9/1988  European Pat. Off. .
63-222248  9/1988  Japan .
1-244335  9/1989  Japan .

Primary Examiner—Hezron E. Williams
Assistant Examiner—Joseph W. Roskos
Attorney, Agent, or Firm—Ronald P. Kananen

[57] ABSTRACT

An odor sensing system is comprised of a sensor cell including a plurality of quartz resonator sensors aligned therein to detect odor by variation of resonance frequencies derived from weight loading on surfaces thereof, a recognition line including a neural network which recognizes data obtained by subtraction between an output signal of the sensor as frequency variation and, a reference signal selected by one of the output signals of the sensor. The sensor cell is thermostatically regulated by circulating thermostatic water therein to maintain the temperature higher than an advance line of the system. A sample to be recognized is supplied to the sensor cell in a form of vapor generated by blowing a standard gas onto the surface of the sample.

30 Claims, 4 Drawing Sheets

ODOR SENSING SYSTEM

BACKGROUND OF THE INVENTION

1. Field of The Invention

The present invention relates generally to an odor sensing system having high recognitivity. Specifically, the present invention relates to an odor sensing system having high recognitivity which can discriminate closely parallel odors.

2. Description of The Background Art

Generally, human sensory tests have been applied for controlling quality of various substances such as food products, drinking products and cosmetics by discriminating odors thereof. Alternatively, human sensory tests have been applied for estimation in environmental and clinical fields. However, human olfaction is varied readily, because it depends on bodily or ambient conditions of the tester. Therefore, in order to obtain objective results constantly, odor sensing systems replacable with human olfaction have been developed.

Commonly, gas sensing systems as such odor sensing systems are well known in the art. For example, Japanese Patent First Publication (not allowed) No. 1-244335 discloses a gas sensing system which imitates human olfaction, i.e., a plurality of gas sensors are employed to receive odor stimulation, then pattern recognition is done. In human olfaction, a variety of odor stimulating patterns are received by a plurality of receptors, then the output patterns from the receptors are recognized in olfactory neural network system to discriminate odors. The aforementioned prior art replaces the receptor by a quartz resonator sensor, and replaces an olfactory neural network system by an artificial neural network system. Odors are discriminated by recognition of a variety of patterns output from a plurality of resonators via a neural network system.

However, many odors which are required to be discriminated are extremely proximate each other, so the sensing system as aforementioned cannot sufficiently distinguish various odors.

Additionally, homogeneity of a supplied sample is apt to fluctuate in the plurality of sensors. Therefore, different results are obtained frequently, even if the same odor is provided to the sensory test.

SUMMARY OF THE INVENTION

It is therefore a principal object of the present invention to provide an odor sensing system which can discriminate closely parallel odors.

It is another object of the present invention to provide an odor sensing system which can obtain constant results.

In order to accomplish the aforementioned and other objects, an odor sensing system for discrimination of closely parallel odors comprises, a sample vapor supply line having a gas supply means to supply gas flow through the system, a mass flow controller connected to the gas supply means to maintain the flow constantly, a cleaning circuit including a switch-over means connected to the mass flow controller allowing the gas to pass through the circuit, and a sampling circuit connected to the mass flow controller and the switch-over means switching between the cleaning circuit and the sampling circuit, the sampling circuit including a plurality of sample vapor generators selectively allowing the gas flow to pass therethrough to generate a sample vapor therein; a signal output line connected to the sample vapor supply line having a plurality of gas sensors to convert the plurality of sample vapors received from the line to a plurality of pattern signals; and a recognition line connected to the signal output line to receive the plurality of signals therefrom, the recognition line having distinction means to calculate respective subtraction between the signals to distinguish differences therebetween, and a discrimination means connected to the distinction means to discriminate odor included in the sample from the subtracted signals.

According to another aspect of the present invention, a method for discriminating odors having closely parallel characteristics comprising the steps of: supplying a gas flow to a plurality of samples to selectively generate a sample vapor therefrom; gathering the selectively generated sample vapors; converting the plurality of sample vapors to a plurality of signals having frequency variation, individually; selecting one of the signals, detecting the selected signal to memorize as a reference signal; detecting the remainder of the signals sequentially: calculating subtraction between the reference signal and the remainder signals respectively, to distinguish a difference therebetween; and discriminating the subtracted signals to recognize odor included in the sample using a pattern algorithm.

The above method may further be implemented including a step of removing odorants present from previous discriminations before supplying the gas flow to the sample.

BRIEF DESCRIPTION OF THE DRAWINGS

The present invention will be understood more fully from the detailed description given herebelow and from the accompanying drawings of the preferred embodiments of the invention. However, the drawings are not intended to imply limitation of the invention to a specific embodiment, but are for explanation and understanding only.

In the drawings:

FIG. 2(*b*) is a sectional view of the sensor cell of FIG. 2(*a*);

FIG. 4(*b*) is a sectional view of vapor generation equipment according to the present invention.

DESCRIPTION OF THE PREFERRED EMBODIMENT

Figure 1:
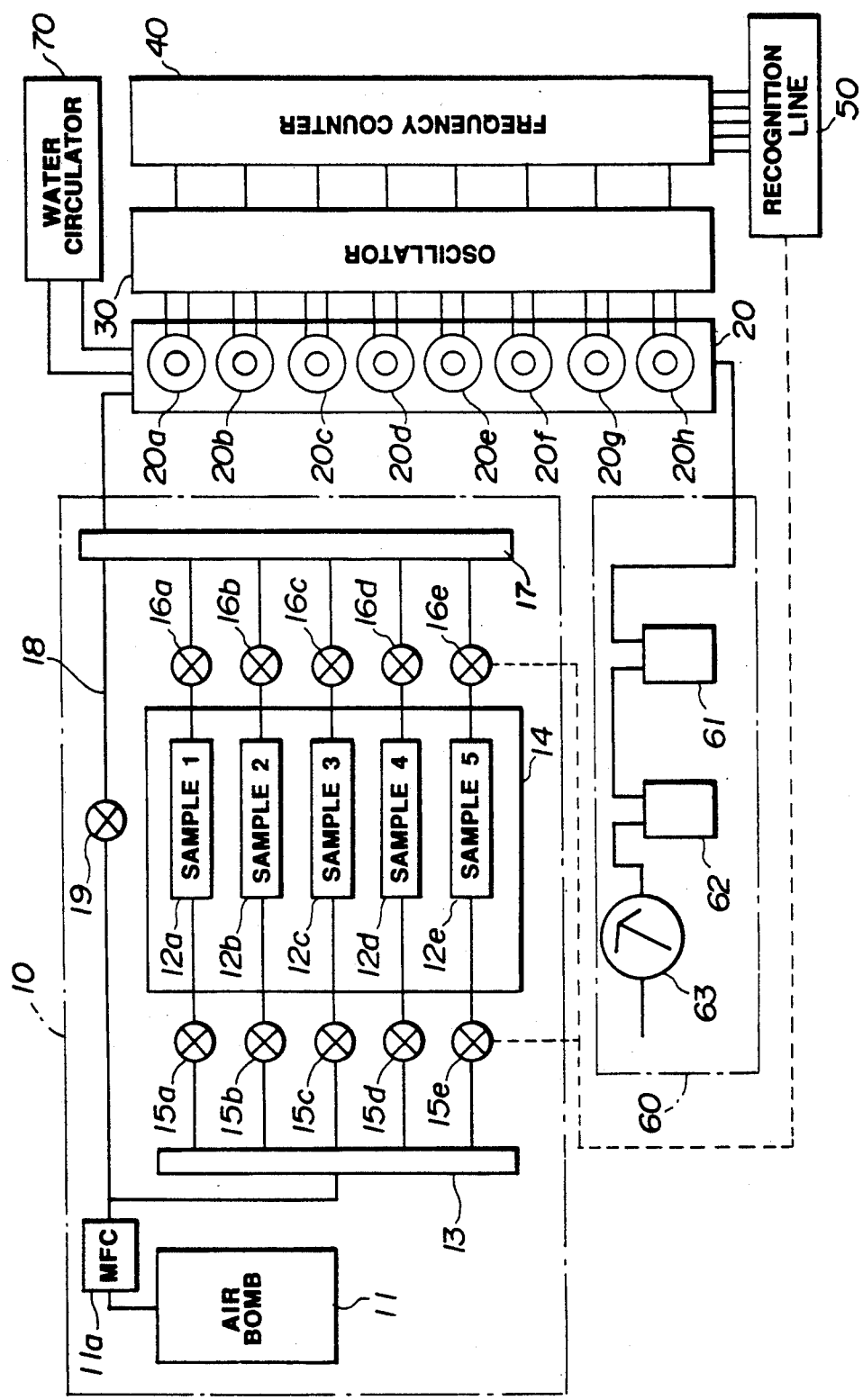
FIG. 1 is a schematic diagram of an odor sensing system according to the present invention.

Referring now to the drawings, particularly to FIG. 1 showing a schematic diagram of an odor sensing system of the present invention, carrier gas is generated in a sample gas supply system 10 by a standard air bomb 11 installed therein. Standard air is used as the carrier gas, to raise reliability of data by constant supply, instead of dried atmospheric air passing through silica gel. Pressure of the standard air bomb 11 is employed as the driving power of gas flow through the system. The carrier gas generated in the air bomb 11 is passed through a mass flow controller 11a, then distributed to sample vapor generators 12a to 12e via a first distributor 13. The mass flow controller 11a is installed to maintain a constant flow rate of the carrier gas through the whole system 10 for improving repeatability of measurement regardless of loading fluctuation. In the sample vapor generators 12a to 12e, a sample vapor is generated from the carrier gas passed therethrough. The sample vapor generators 12a to 12e are thermostatically regulated in a thermostat 14. The carrier gas is entered into the sample vapor generators 12a to 12e by selective opening of solenoid valves 15a to 15e, and entered into a second distributor 17 by selective opening of solenoid valves 16a to 16e, correspondingly. One sample vapor is selected by a pair of valves which are associated with each other, 15a and 16a. A cleaning circuit 18 is formed between the mass flow controller 11a and the second distributor 17 allowing carrier gas to pass through directly from the standard air bomb 11 via a solenoid valve 19 positioned in the circuit 18, before the sample gas enters the second distributor 17.

Eight quartz resonator sensors 20a to 20h are aligned to form a sensor array in the sensor cell 20. Firstly, the carrier gas is supplied to the sensor cell 20 from the standard air bomb 11 via the second distributor 17 to remove the odorant from the cell 20, then the sample gas selected by the pair of valves, for example, 15a and 16a, is input to the sensor cell 20 via the second distributor 17. The sensor cell 20 is connected to a Colpitts oscillator 30 having 8 independent channels to be connected with corresponding quartz resonator sensors. Oscillated signals output from each channel are input to a frequency counter 40, then frequency alteration of each quartz resonator sensor is measured. The frequency of each of the quartz resonators is measured concurrently and in parallel. Sampling may be accomplished in one second.

The measured signal is input into a recognition line 50 comprised by a microcomputer device connected to the frequency counter 40. The output signal of the frequency counter 40 is read by a microcomputer device from an I/O port thereof via an interface board, then the signal is input into a neural network system programmed therein to recognize odor included in the sample. The recognition line 50 also controls solenoid valves of the sample gas supply system 10 as aforementioned via the interface board and selective opening of the valves is automatically controlled.

Sample gas through the sensor cell 20 is fed into an exhaust line 60 to eject gas from the sensing system. A buffer means 61 is installed between an outlet port of the sensor cell 20 and a trap means 62 for preventing back flow of a solution, water for example, from the trap means 62 to the sensor cell 20. The buffer means 61 may be composed of a sampling tube and a conduit, formed of a hard material, penetrating the tube. The trap means 62 includes a vessel with a solution such as water or solvent therein to trap gas into the solution. The odorant included in the gas is dissolved by bubbling in the solution, thus, leakage of odorant to the outside ambient can be prevented. Mass flow of the gas in the sensor cell 20 is measured by a mass flow meter 63 installed to an outlet port of the trap means 62 for accurate measurement. A volume flow meter may be preferred as the flow meter 63, in this case an outlet port of the volume flow meter must be positioned at an outlet port of the system because the meter cannot operate accurately in a loaded (closed) condition. Mass flow measured by the flow meter is regulated by a pressure reducing valve of the standard air bomb 11 in the sample gas supply system 10. Thus, the gas from the sensor cell 20 is blown off in ambient air from the mass flow meter 63.

The sensor cell 20 is thermostatically regulated by a water circulator 70.

Figure 2A:
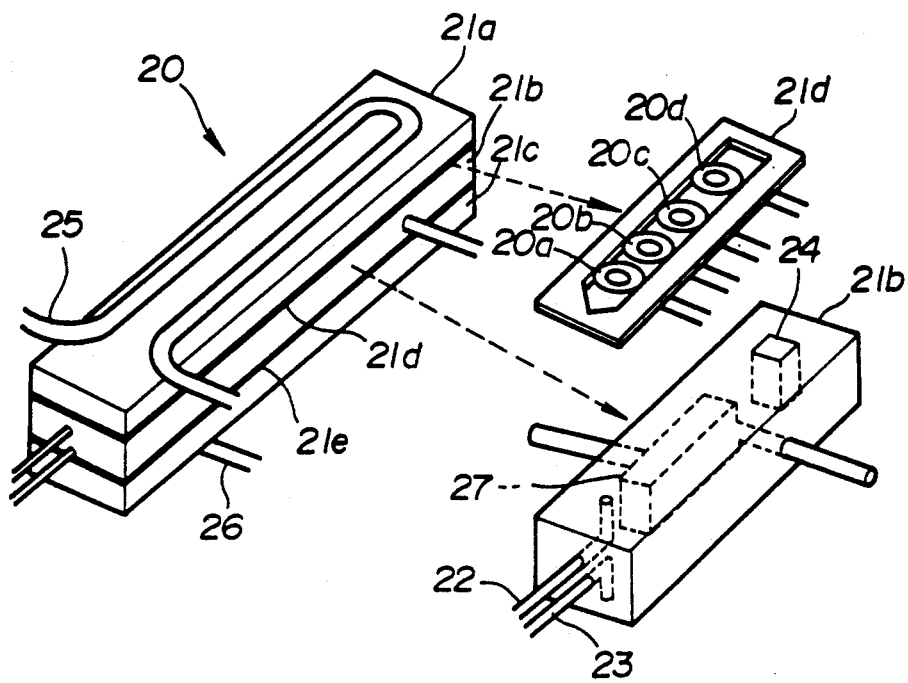
FIG. 2(*a*) is an exploded perspective view of a sensor cell according to the present invention.
Figure 2B:
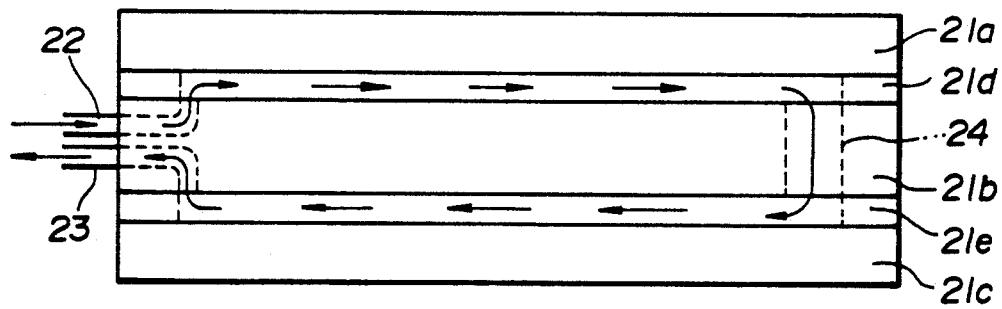

FIGS. 2(a) and 2(b) show the structure of the sensor cell 20. The sensor cell 20 is composed of three layers 21a, 21b and 21c formed of metallic material such as stainless steel, respectively. A first sensor plate 21d and a second sensor plate 21e having hollows respectively formed therein of fluorine containing resin, are sandwiched between the layers 21a and 21b, and the layers 21b and 21c, respectively. In the hollow of the first sensor plate 21d, the quartz resonator sensors 20a to 20d are aligned to form a first sensor array, and in the hollow of the second sensor plate 21e, the quartz resonator sensors 20e to 20h are aligned to form a second sensor array. An inlet port 22 connected to the outlet port of the second distributor 17, an outlet port 23 connected to the buffer means 61 of the exhaust line 60, and an air hole 24 for the carrier or the sample gas penetrating the second layer 21b are included in the second layer 21b. The inlet port 22 is opened in an end of the first sensor plate 21d, and the outlet port 23 is opened in an end of the second sensor plate 21e. The air hole 24 communicates with the other ends of the first sensor plate 21d and the second sensor plate 21e. Thus, carrier and sample gas flow in the sensor cell 20, as shown in FIG. 2(b), is established. A first water conduit 25 is mounted on the upper surface of the first layer 21a, a second water conduit 26 is mounted on the lower surface of the third layer 21c, and a water pool 27 is installed in the second layer 21b, to circulate water from the water circulator 70 for thermostatic regulation of the sensor cell 20. For easy assembly and removal, the quartz resonator sensors 20a to 20h may be inserted to the sensor cell 20 by being individually installed in a casing formed of stainless steel. The casing may then be positioned at a location corresponding to the sensor cell 20 and secured thereto by a board formed of acrylic resin, for example, and screws. This allows sensors, which may be reused many times, to be easily replaced or cleaned, for example.

Figure 3:
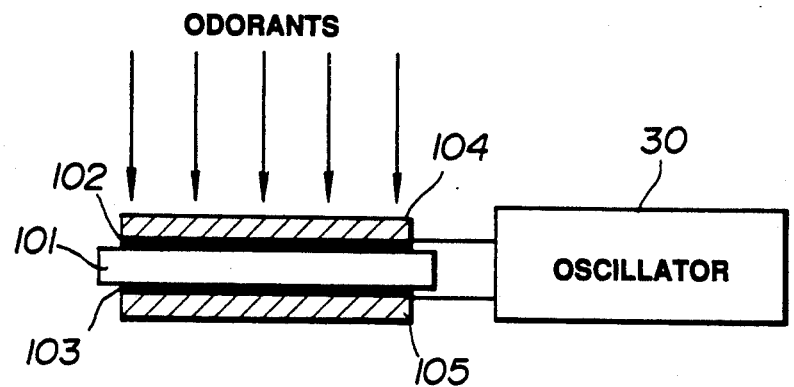
FIG. 3 is a sectional view of a quartz resonator sensor installed to the sensor cell of the present invention.

Referring now to FIG. 3 showing a structure of the quartz resonator sensor of the above-mentioned, a quartz resonator 101 having an AT-cut and 10.14 MHz of fundamental resonance frequency is held between electrodes 102 and 103. Each of the electrodes 102 and 103 is connected to the corresponding oscillation circuit of the Colpitts oscillator 30. Odorant adsorbing membranes 104 and 105 are applied on the surface of the electrodes, to the side opposite which the sensor is applied, respectively. Each membrane has different adsorbing characteristics. If the thickness of the membrane applied to the quartz resonator 101 becomes too thick, elasticity of the resonator is deteriorated which causes quenching of oscillation. Therefore, application of the membranes is accomplished by regulating a Q value (quality factor) to be higher than 5400 using an impedance analyzer referring to alteration of resonance frequency.

Oscillation of the quartz resonator sensor depends on the adsorbability of the membrane. Stationary phases for gas chromatography (GC), celluloses, and lipid materials are desirable for sufficient discrimination of closely parallel odors.

Figure 4A:
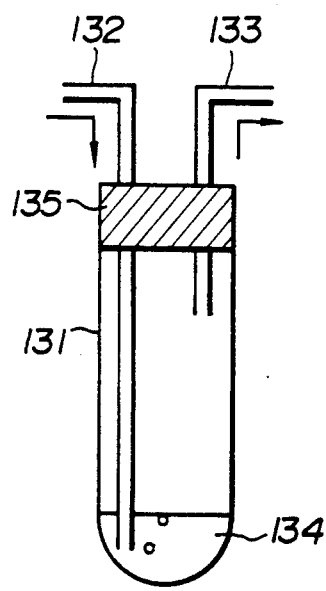
FIG. 4(*a*) is a sectional view of vapor generation equipment according to the prior art.
Figure 4B:
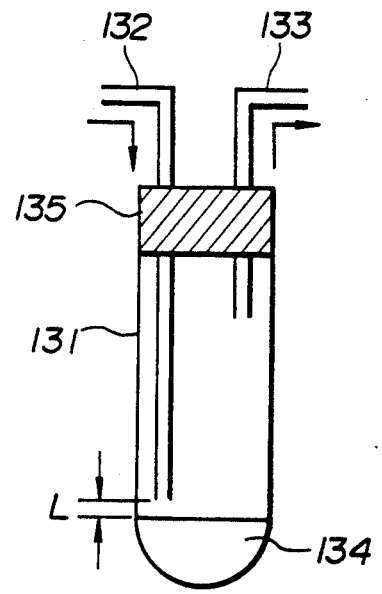

Referring now to FIGS. 4(a) and 4(b) showing structures of vapor generation equipment installed in the sample vapor generators, the carrier gas is provided from the standard air bomb to a sample vessel 131 via an injection nozzle 132, and is output with the sample vapor generated in the vessel 131 toward the sensor cell via an outlet nozzle 133. Sample solution 134 is prepared in the vessel 131 beforehand. In the prior art, as shown in FIG. 4(a), the injection nozzle 132 is dipped into the solution 134 directly, so the carrier gas is injected into the solution 134. The sample vapor is generated by bubbling the carrier gas into the solution 134. Whereas, in the present invention, the injection nozzle 132 is spaced apart from the surface of the sample solution 134 by a distance L as shown in FIG. 4(b). The sample vapor is generated naturally by blowing the carrier gas to the surface of the solution 134. The injection and outlet nozzles 132 and 133 are tightly secured to the sample vessel 131 by a suitable cock 135.

Figure 5:
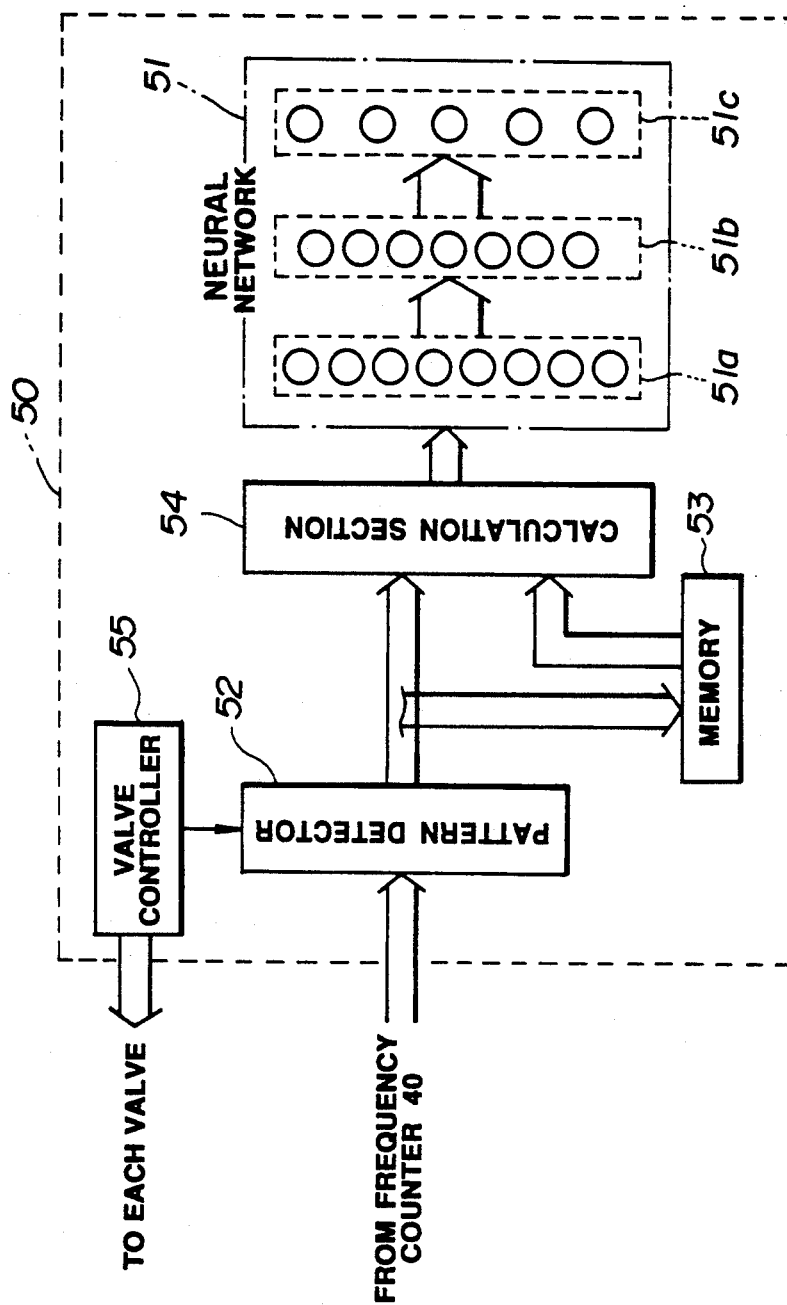
FIG. 5 is a schematic diagram of a recognition line included in the odor sensing system according to the present invention.

FIG. 5 is a schematic diagram showing the recognition line 50, including a neural network 51 having a three-layer structure. The neural network 51 is composed of eight input layers 51a corresponding to the number of the sensors, seven hidden layers 51b, and five output layers 51c corresponding to numbers of the samples. One signal is selected from the output signals of the frequency counter 40. Then, the selected signal is input into a pattern detector 52 and memorized in a memory 53 as a reference signal. The sample signal from the frequency counter 40 is input to the detector 52, and fed to a calculation section 54. In the calculation section 54, subtraction of the reference signal and the sample signal is done. Substracted data are input into each of the input layers 51a of the neural network 51. Thus, the odor of the sample is recognized in the neural network 51. Recognition is automatically accomplished by valve control of each solenoid valve in the sample gas supply system 10 via a valve controller 55 also programmed in the recognition line 50.

During operation of the odor sensing system, odorant molecules included in the atmosphere are adsorbed by the adsorbing membrane applied on the quartz resonator sensor. Then, the surface of the resonator sensor is slightly weighted allowing a resonance frequency thereof to vary in an oscillator circuit. Commonly, when an AT-cut quartz resonator adsorbs a substance having a weight of $\Delta M$, resonator frequency variation $\Delta f$ is calculated by Sauerbrey's formula as follows;

$$\Delta f = -2.3 \times 10^{-6} \times f^2 \times \Delta M / A \quad (1)$$

wherein A is the area of an electrode (cm$^2$)

The above-recited formula (1) shows that a resonance frequency is varied proportionally with weight of the adsorbed substance, i.e., resonance frequency is reduced according to the weight loading in the oscillator circuit. The variation rate of the resonance frequency defines a sensor output. The odorant molecules adsorbed on the membrane are removed by passing standard air through the sensor to recover the initial resonance frequency after measurement of the odor.

In advance of measurement, initial training of the neural network is done to teach the system to recognize odors automatically using a back-propagation algorithm. Five samples are measured 10 times and obtained data is used for the initial training. The initial training is done 20,000 times. Initial values of a binding weight coefficient among three layers of the neural network are obtained by this training. In order to prevent data drift derived from certain kinds of factors such as time progressing, the weight coefficient is compensated by 500 times of adaptive training (using a similar back-propagation algorithm) at every round of measurement of the five samples. Recognitivity is defined by dividing the number of right answers by the total number of measurements at every 10 sets of recognitions. The neural network is more adaptable compared to conventional pattern recognition algorithms because the data are compensated by the training at every set of measurements according to environmental changes. Furthermore, the neural network can recognize odors in a near-human fashion, because it imitates information processing in the human brain. Recognitivity is raised by subtraction between the output signal of the samples and the reference signal selected from one of the samples. The close difference of odors is emphasized by this subtraction.

Measurement of odor included in the samples are accomplished after initial training of the neural network. Each pair of solenoid valves (for example, 15a and 16a. 15b and 16b of FIG. 1) is repeatedly opened sequentially before the samples are put into the sample vessels of the sample vapor generators 12a to 12e.

Standard air is fed through the line to remove the odorant from each solenoid valve. Then, five samples, for example, are put into the sample vessels, respectively. Odorant adsorbed by the sensor corresponding to one sample is removed by feeding standard air through the cleaning circuit 18 to the sensor cell 20 by opening the solenoid valve 19, for 60 seconds or so. After cleaning, gas including sample vapor is fed through the quartz resonator sensor for 30 seconds. The output signal of the sensor is detected by the pattern detector 52 of the recognition line 50. The detected signal is memorized in the memory 53 as a reference signal pattern. After defining the reference signal pattern, each sample is measured by cleaning the sensor, feeding gas, and detecting output pattern, respectively. The subtraction between the reference signal pattern and the detected signal patterns of each sample are calculated for input into the neural network 51 for recognition of odors. The aforementioned processing of five samples is repeated 10 times to obtain recognitivity as previously mentioned.

Several functions are determined in order to obtain high recognition probability.

First, duration of a sample vapor supply is determined as in the following Example 1.

EXAMPLE 1

Identical samples were put into each sample vapor generator. The sample vapor was supplied for a minute in a flow rate of 25 ml/min. Then the output data after 10 to 60 seconds were measured. Data stability of the obtained data was estimated by multivariate analysis. From the results, it was found that data fluctuation is increased according to time progressing, and homogeneity of each line of vapor generators is decreased concurrently. Therefore, from the results, an optimal duration of sample vapor supply is determined at 30 sec. Concurrently, data is measured at the time. Thus, the recognition reliability can be raised while maintaining homogeneity of the line.

Generation of the sample vapor is regulated by spacing the injection nozzle 132 apart from the surface of the sample solution 134 to obtain the same characteristics for the same sample always in any of the vapor generators. For establishment of homogeneity at every vapor generator, the sample vapor generated naturally is more suitable than the conventional method in which vapor is generated by bubbling in solution. It is also effective to maintain the distance L between an open end of the injection nozzle and the surface of the solution constantly for reducing the data fluctuation. The suitable distance L is determined by following Example 2.

EXAMPLE 2

Identical samples were put into five test tubes of $21\phi \times 200$ mm having rims. Distance L was varied in each test tubes, and output signals of eight sensors were measured. The obtained results are shown in Table 1. The output signals are indicated as vectors $|v|$ having eight dimensions.

TABLE 1

| | Relationship between L and $|v|$ | | | | |
|---|---|---|---|---|---|
| No. of Tubes | 1 | 2 | 3 | 4 | 5 |
| L (mm) | 8 | 50 | 92 | 8 | 8 |
| Sample Amount (cc) | 25 | 15 | 5 | 15 | 5 |
| $|v|$ | 3991 | 3462 | 2456 | 3797 | 3582 |

Output signals of the test tubes 1 and 5 are sufficiently larger than the others regardless of varying the sample amount. Therefore, the sample amount does not influence the output signals. A preferable sample amount is 25 cc from the largest value of the output (tube 1). In the present invention, the optimal sample amount is determined to 20 cc, and the most preferred distance L is determined to be 8 mm. The distance L is maintained constantly in all of the sample vessels to obtain accurate result always.

The flow rate of the gas regulated by the mass flow controller 11a is determined to about 50 ml/min. In the present invention, the volume of the head space of the sample solution becomes about 30 ml and measurement duration is determined to 30 seconds. So, a flow rate larger than 60 ml/min. causes all the air in the head space of the solution pushing out of the sample vessel. Therefore, the suitable flow rate is less than 60 ml/min. The optimal flow rate is determined to about 50 ml/min.

Temperature through the system is regulated by water circulation around the sample vapor generators of the sample vapor supplying line 10. Thermostatic water (fluctuating in a range of ±0.5° C.) is circulated from the water circulator 70 to the sensor cell 20 via the thermostat 14 in which vapor generators are dipped. Temperature distribution in the vapor generator, middle pass of the system, and the sensor cell are determined as follows.

| Vapor generator about 16° C. | Middle of the system about 18° C. | Sensor Cell about 20° C. |
|---|---|---|

Coagulation of vapor in lines of the system can be prevented by this temperature distribution. Therefore, temperature cannot significantly influence adsorption of the adsorbing membrane applied on the sensor. Accordingly, a fluctuation coefficient of measurement, calculated by dividing a standard deviation of the sensor output by the average of the sensor output, restrains fluctuation within a small value. In the experiment, the coefficient of the present invention was 1% compared with that of the prior art, which was 2 to 3% as the conventional system is not thermostatically regulated.

Suitable materials for the adsorbing membrane are selected by cluster analysis method and the Wilks' lambda statistic F, as shown in Table 2.

TABLE 2

| | Membrane for the Sensor | |
|---|---|---|
| No. | Membrane | Classification |
| 1 | Dioleyl Phosphatidylserin | Lipid |
| 2 | Sphingomyelin (Egg) | Lipid |
| 3 | Lecithin (Egg) | Lipid |
| 4 | Cholesterol | Sterol |
| 5 | Perfluorinated Bilayer | Synthesized Lipid |
| 6 | Polyethylene glycol (20M) | GC |
| 7 | Ethyl cellulose | Cellulose |
| 8 | Acetyl cellulose | Cellulose |

EXAMPLE 3

Discrimination of odorants was examined using the membranes shown in Table 2.

For samples, five Japanese whiskeys having closely parallel aromas were used. Each sample was passed through the system 10 times. The initial training of the neutral network was done 20,000 times using the obtained data. In order to compensate data drift, adaptive training was performed 500 times at every round of measurement. Recognitivity was defined as the ratio of the number of right answers against that of the total trials. The obtained results are shown in Table 3. The matrix number indicates the number of times which the sample was recognized as the corresponding sample. The average recognitivity was 94%.

TABLE 3

| | Odor Discrimination Results | | | | |
|---|---|---|---|---|---|
| | Discriminated category | | | | |
| No. | 1 | 2 | 3 | 4 | 5 |
| 1 | 10 | 0 | 0 | 0 | 0 |
| 2 | 0 | 9 | 1 | 0 | 0 |
| 3 | 0 | 1 | 9 | 0 | 0 |
| 4 | 0 | 0 | 0 | 10 | 0 |
| 5 | 0 | 0 | 0 | 1 | 9 |

Additionally, cleaning of a flow line (the vapor supply line, the sensor, the recognition line and the exhaust line) and that of the solenoid valves both accomplished beforehand of measurement can further raise recognition reliability by restraining influences between measurement rounds. In the step of cleaning the solenoid valves, employment of a flexible heater coiled around the valve may be suitable for easy removal of the odorant from the valve by heating it.

According to the present invention, closely parallel odors can be discriminated by emphasizing the difference therebetween using the subtraction value between the plurality of output signals of the quartz resonator sensors and the reference signal.

Further to say, the sample vapor is generated naturally by blowing gas on the surface of a sample solution. Therefore, homogeneity of the sample vapor at every vapor generator can be established. Accordingly, high reliability of recognition can be established.

Additionall, standard air is passed through the flow line and the valves before of measurement for cleaning thereof. This also leads high reliability of odor recognition.

Furthermore, thermostatic regulation through the whole system is accomplished by circulating water through the the vapor generators and the sensor cell to maintain temperature thereof higher than the vapor supply line. Therefore, the sample vapor is not coagulated, so high reliability of recognition can be obtained.

While the present invention has been disclosed in terms of the preferred embodiment in order to facilitate a better understanding of the invention, it should be appreciated that the invention can be embodied in various ways without departing from the principle of the invention. Therefore, the invention should be understood to include all possible embodiments and modification to the shown embodiments which can be embodied without departing from the principle of the inventions as set forth in the appended claims.

What is claimed is:

1. An odor sensing system for discrimination of closely parallel odors, said system comprising:
   a sample vapor supply line having a gas supply means to supply gas flow through said system, a mass flow controller connected to said gas supply means to maintain said flow constantly, a cleaning circuit including a switch-over means connected to said mass flow controller allowing said gas flow to pass through said circuit, and a sampling circuit connected to said mass flow controller, said switch-over means switching between said cleaning circuit and said sampling circuit, said sampling circuit including a plurality of sample vapor generators selectively allowing said gas flow to pass therethrough to generate a sample vapor therein,
   a signal output line connected to said sample vapor supply line having a plurality of gas sensors to convert said plurality of sample vapors received from said line to a plurality of pattern signals; and
   a recognition line connected to said signal output line to receive said plurality of signals therefrom, said recognition line having distinction means to calculate a respective subtraction between said signals to distinguish differences therebetween, and a discrimination means connected to said distinction means to discriminate odor included in said sample from said subtracted signals.

2. An odor sensing system as set forth in claim 1, wherein said system further includes thermostatic regulation means to maintain a temperature essentially surrounding said signal output line higher than that of said sample vapor supply line for establishing homogeneity of said sample vapor to be passed therethrough by preventing coagulation of said sample vapor in said system.

3. An odor sensing system as set forth in claim 2, wherein said thermostatic regulation is accomplished by circulating water through said sample vapor supply line and said signal output line, said water being regulated to a desired temperature.

4. An odor sensing system as set forth in claim 1, wherein said system further includes an exhaust line connected to said output line to exhaust said sample vapor from said system toward an outside ambient.

5. An odor sensing system as set forth in claim 1, wherein said sample vapor is generated by blowing said gas flow to the surface of said sample in said sample vapor generator, if said sample is in liquid form.

6. An odor sensing system as set forth in claim 5, wherein said gas flow is blown from a blow end installed in said sample vapor generator, keeping a desired distance between said blow end and said surface of the sample constant.

7. An odor sensing system as set forth in claim 6, wherein said distance is determined to 8 mm.

8. An odor sensing system as set forth in claim 1, wherein said gas flow supplied from said gas supply means is standard air.

9. An odor sensing system as set forth in claim 1, wherein said mass flow controller controls said gas flow in a flow rate of less than 60 ml/min.

10. An odor sensing system as set forth in claim 9, wherein said flow rate is determined to 50 ml/min.

11. An odor sensing system as set forth in claim 1, wherein said gas sensor included in said signal output line is a quartz resonator sensor having a pair of membranes, said quartz resonator sensor held therebetween to adsorb an odorant included in said sample vapor.

12. An odor sensing system as set forth in claim 11, wherein said quartz resonator sensor is movable from its desired position in said signal output line by positioning in a metallic casing.

13. An odor sensing system as set forth in claim 11, wherein said membrane is selected from the group consisting of gas chromatographic stationary phases, celluloses, and lipid materials.

14. An odor sensing system as set forth in claim 11, wherein said membrane is selected from the group consisting of dioleyl phosphatidylserin, sphingomyelin, lecithin, cholesterol, perfluorinated bilayer, polyethyleneglycol, ethyl cellulose, and acetyl cellulose.

15. An odor sensing system as set forth in claim 1, wherein said cleaning circuit is switched over before said sample is put into said sample vapor generator to clean said signal output line.

16. An odor sensing system as set forth in claim 1, wherein said switch-over means is a solenoid valve.

17. An odor sensing system as set forth in claim 1, wherein said plurality of sample vapor generators are passed through by said gas flow before said sample is put thereinto for cleaning thereof.

18. An odor sensing system as set forth in claim 17, wherein said gas flow is heated.

19. A method for discriminating odors having closely parallel characteristics comprising the steps of:
   supplying a gas flow to a plurality of samples to selectively generate a sample vapor therefrom;
   gathering said selectively generated sample vapors;
   converting said plurality of sample vapors to a plurality of signals having a frequency variation, individually;
   selecting one of said signals,
   detecting said selected signal to memorize as a reference signal,
   detecting the remainder of said signals sequentially,
   calculating a subtraction between said reference signal and said remainder signals, respectively to distinguish a difference therebetween, and
   discriminating said subtracted signals to recognize odor included in said sample using a pattern algorithm.

20. A method as set forth in claim 19 further comprising the step of removing odorants present from previous discriminations before supplying said gas flow to said sample.

21. A method as set forth in claim 19 further comprising the step of thermostatically regulating a conversion temperature of said sample vapor higher than a generating temperature for establishing homogeneity of said sample vapor to be passed therethrough by preventing coagulation thereof.

22. A method as set forth in claim 21, wherein said thermostatic regulation is accomplished by circulating water regulated to a desired temperature for said generation and said conversion, respectively.

23. A method as set forth in claim 19, wherein said step of supplying said gas flow including a step of blowing said gas flow to the surface of said sample, if said sample is in liquid form.

24. A method as set forth in claim 23, wherein said blowing is done keeping a desired distance from the surface of the sample constant.

25. A method as set forth in claim 24, wherein said distance is determined to 8 mm.

26. A method as set forth in claim 19, wherein said step of supplying said gas flow is controlled by a mass flow controller at a flow rate of less than 60 ml/min.

27. A method as set forth in claim 26, wherein said flow rate is determined to 50 ml/min.

28. A method as set forth in claim 19, wherein said step of converting is accomplished by a plurality of quartz resonator sensors, each sensor having a pair of membranes, said quartz resonator sensor held therebetween to adsorb said odorant included in said sample vapor.

29. A method as set forth in claim 28, wherein said membrane is selected from the group consisting of gas chromatographic stationary phases, celluloses, and lipid materials.

30. A method as set forth in claim 28, wherein said membrane is selected from the group consisting of dioleyl phosphatidyleerin, sphingomyelin, lecithin, cholesterol, perfluorinated bilayer, polyethyleneglycol, ethyl cellulose, and acetyl cellulose.

* * * * *